United States Patent [19]

Beyer et al.

[11] Patent Number: 5,354,293
[45] Date of Patent: Oct. 11, 1994

[54] APPARATUS FOR THE ISOTROPIC IRRADIATION OF CAVITY WALLS

[75] Inventors: Wolfgang Beyer, Munich; Armin Heinze, Ismaning; Dieter Jocham, Munich; Klaus Schmitt, Remshalden-Grunbach; Eberhard Unsoeld, Oberschleissheim, all of Fed. Rep. of Germany

[73] Assignee: Gesellschaft fur Strahlen-und Umweltforschung mbH, Neuherberg, Fed. Rep. of Germany

[21] Appl. No.: 833,827

[22] Filed: Feb. 13, 1992

Related U.S. Application Data

[63] Continuation of Ser. No. 620,899, Dec. 3, 1990, abandoned.

[30] Foreign Application Priority Data

Dec. 18, 1989 [DE] Fed. Rep. of Germany ....... 3941705

[51] Int. Cl.$^5$ ............................................. A61N 5/06
[52] U.S. Cl. ...................................... 606/15; 606/16; 606/17; 607/88; 607/92
[58] Field of Search ...................................... 606/6–18; 128/395, 397, 398; 607/88–92

[56] References Cited

U.S. PATENT DOCUMENTS

| | | | |
|---|---|---|---|
| 4,470,407 | 9/1984 | Hassein et al. | 128/6 |
| 4,612,938 | 9/1986 | Dietrich et al. | 606/12 |
| 4,625,724 | 12/1986 | Suzuki et al. | 606/8 |
| 4,878,492 | 11/1989 | Sinofsky et al. | 606/13 |
| 4,998,930 | 3/1991 | Lundahl | 606/15 |

FOREIGN PATENT DOCUMENTS 0232511 8/1987 European Pat. Off. .

*Primary Examiner*—David M. Shay
*Attorney, Agent, or Firm*—Klaus J. Bach

[57] ABSTRACT

An apparatus for the isotropic irradiation of cavity walls includes in a first channel of a catheter a light conducting fiber which has a cortically shaped tip for deflecting a light beam radially outwardly through a transparent portion of the catheter and a resiliently expandable sleeve tightly disposed around the catheter and having its interior in communication by a second channel with a fluid supply for expanding the sleeve so as form a light scattering structure whose scattering characteristics are adjustable dependent on the degree of sleeve expansion.

5 Claims, 4 Drawing Sheets

APPARATUS FOR THE ISOTROPIC IRRADIATION OF CAVITY WALLS

This application is a continuation of application Ser. No. 07/620,899, filed Dec. 3, 1990, now abandoned.

BACKGROUND OF THE INVENTION

The invention relates to apparatus for the isotropic irradiation of the walls of cavities, especially spherical cavities, by means of a catheter containing a light conducting fiber and a deformable sleeve which is expandable by admission of a fluid.

Such apparatus are utilized for the illumination of the walls of cavities such as hollow organs. It is important that the light is uniformly distributed over the whole cavity walls.

Uniform distribution of the light radiation is a necessity, for example, in connection with internal photodynamic therapy, by means of laser light, of photosensitized tumors. A locally insufficient irradiation dosis does not completely destroy the tumor and leads to recurrences while excessive irradiation doses damage healthy wall areas. The tolerance range is generally only relatively small.

U.S. Pat. No. 4,612,938 discloses an apparatus which includes a light conducting glass fiber which is insertable into a spherical organ cavity such as a bladder in such a manner that its end is disposed centrally therein. For uniform scattering of the light the organ is filled with a dispersion liquid. A similar apparatus is described by D. Joeham et al. in "Porphyrin Localization and Treatment of Tumors", New York: Alan R. Liss, June 1984, pages 249 to 256.

In "Photochemistry and Photobiology" 46, No. 5, 1987, pages 619 to 624, W. M. Star et al. utilize for cavity irradiation a centrally arranged radiation emitter with spherical emission characteristics.

The first arrangement however requires high centering accuracy for the light emitting end of the glass fiber. Often such accurate positioning cannot be achieved particularly in situations in which the irradiation equipment is to be inserted into the hollow organ through a narrow catheter. In the second case the catheter itself generates shadows which result in insufficient irradiation of the organ wall areas near the axis of the catheter since the emitter is small relative to the diameter of the catheter.

It is the principal object of the present invention to provide an apparatus for the irradiation of cavity walls such as organs which provides for highly spherical emission characteristics especially with regard to the back portion of the cavity, that is, adjacent a catheter through which the radiation is introduced into the cavity and which is easily insertable through narrow openings in the organs or passages leading to the organ cavities.

SUMMARY OF THE INVENTION

In an apparatus for the isotropic irradiation of cavity walls, particularly of human organs, a catheter includes a light conducting fiber movably arranged in a first channel and provided with a conically shaped tip adapted to deflect light supplied through the conductor essentially radially outwardly through a transparent catheter section which is tightly surrounded by a resiliently expandable sleeve. A second channel is provided which is in communication with the sleeve interior for admitting a fluid thereto to expand the sleeve so as to form a light scattering structure for uniform distribution of the light emitted from the light conductor tip. Light scattering may be provided for either by the fluid or by the sleeve itself. Also, a positioning balloon may be provided which may be filled with a clear fluid and which is adapted to center the catheter in the cavity whose walls are to be irradiated or illuminated.

With the apparatus according to the present invention a central scattering body is formed which is substantially larger in diameter than the catheter and, as a result, is capable of adequate irradiation of the cavity wall areas adjacent the axis of the catheter.

Furthermore the radiation scattering characteristics can be influenced or adjusted by the degree to which the scattering body is filled. This permits control of the isotropy or of a desired anisotropy of the emission characteristics which may be desirable to permit adaption to certain cavity shapes. Also the part of the light which is reflected from the cavity walls contributes to a uniform overall light distribution.

SHORT DESCRIPTION OF THE DRAWINGS

FIG. 1 schematically shows the apparatus according to the invention;

DESCRIPTION OF THE PREFERRED EMBODIMENT

Figure 1:
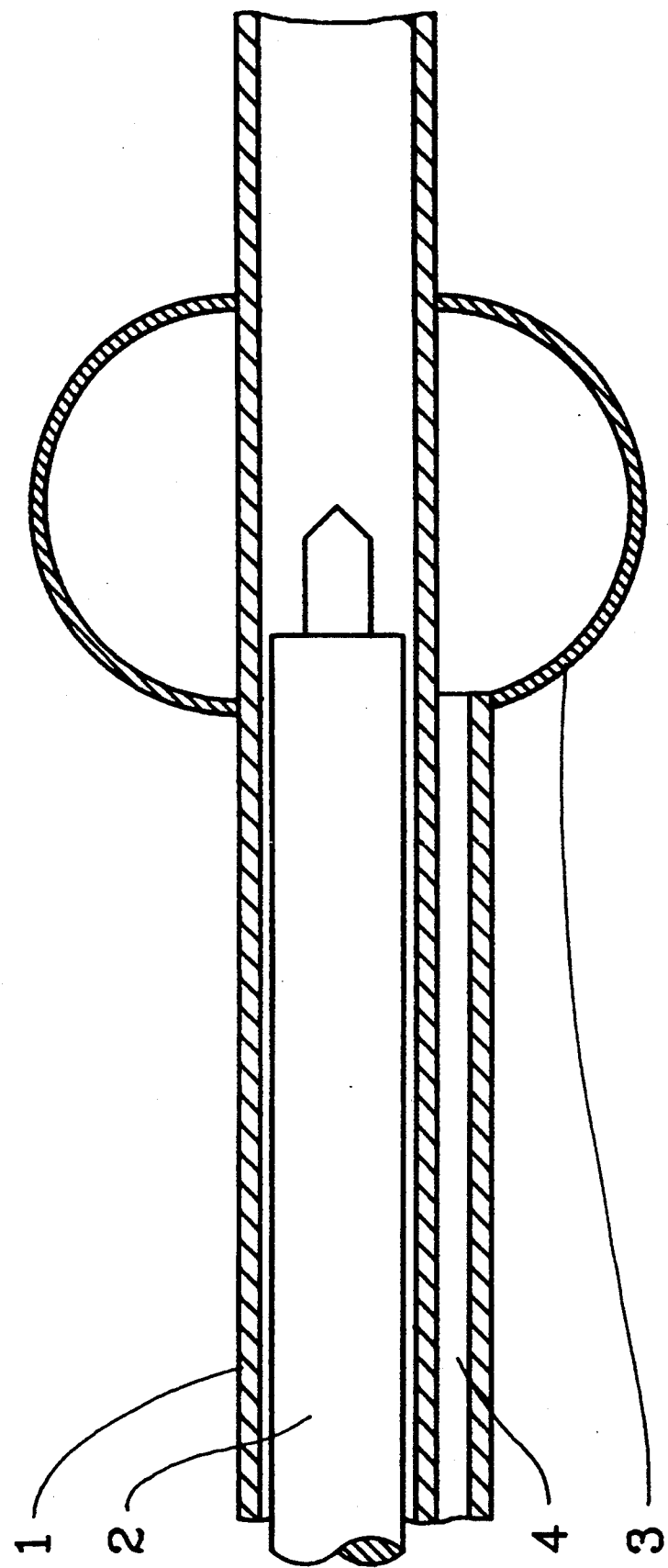

An apparatus as shown in FIG. 1 consists of a transparent catheter 1 in which a glass fiber 2 is inserted such that the fiber tip is disposed in the center of an organ when the catheter is introduced. For position control the fiber and the catheter may be marked or a mechanical stop may be provided.

The catheter can be rinsed or flushed by a clear liquid. In the area of the fiber tip location a resilient sleeve 3 is disposed around the catheter which sleeve may be filled by a fluid 4a through a line 4 such that the sleeve expands with the fiber tip in the center thereof.

Figure 2:
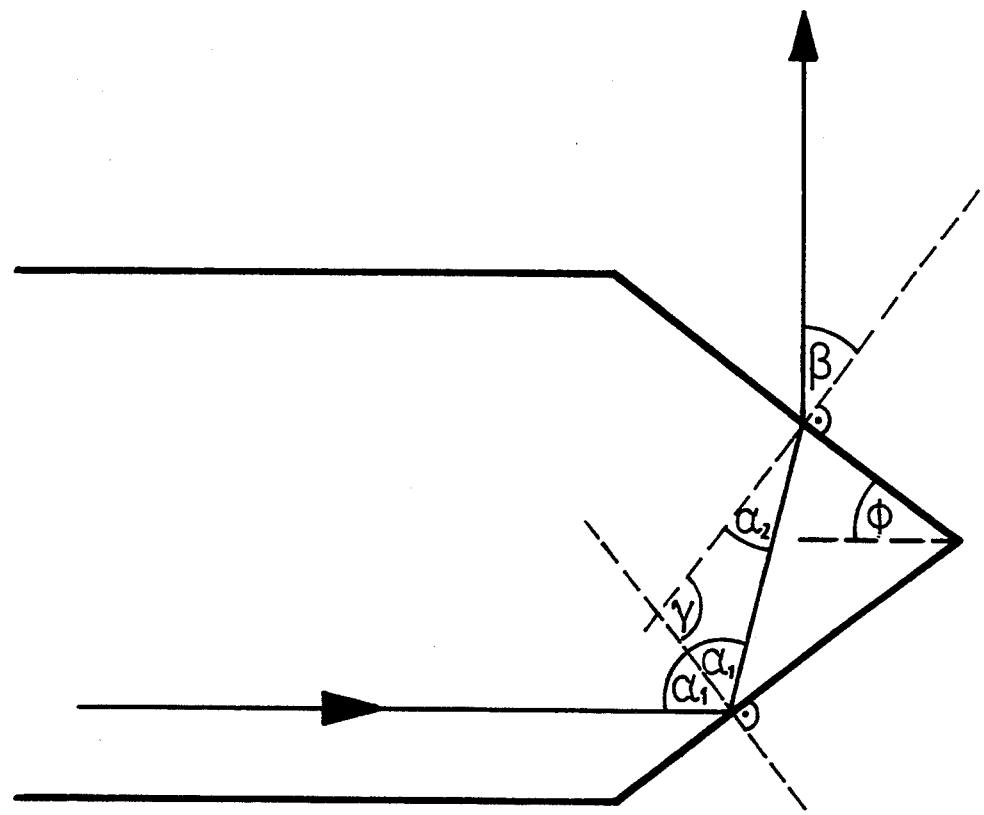
FIG. 2 shows schematically a radiation path at the tip of the light conductor.

FIG. 2 shows the fiber tip with a light beam path on the basis of which the optimum tip cone angle is calculated.

The light leaves the fiber tip preferably at an angle of 90° with respect to the fiber axis. To achieve this the fiber tip has the shape of a cone. The required cone angle is derived on the basis of the following consideration. First, the light beam is totally reflected at one side of the cone and is subsequently refracted at the opposite side. Using the designations of FIG. 2 the following equations apply:

$$\alpha_1 = 90° - \phi$$

and $$\gamma = 180° - 1\phi$$

further $$\alpha_2 = 3\phi - 90°$$

For a beam deflection of 90°, the angle $\beta$ must be:

$\beta = \phi$

With the law of refraction, the following relationship is obtained:

$$\frac{\sin \beta}{\sin \alpha_2} = \frac{\sin \phi}{\cos 3\phi} = n$$

From these conditions half the cone angle, that is, $\phi$, is calculated as 38.1° using a fraction index of $n=1.5$.

Emanating from the fiber tip the light passes through the transparent wall of the catheter 1 into a dispersion or scattering body 1 whose purpose it is to distribute the light over the inner wall surfaces defining the organ cavity. The scattering body consists of a sleeve 3 such as a catheter bottom which is fastened to the catheter and which is positioned by the catheter in the center of the cavity of an organ. The catheter is inserted with an empty balloon, that is, with the sleeve disposed tightly around the catheter. When the catheter is positioned in the organ cavity, the sleeve is filled by way of fluid supply line 4.

Light distribution is achieved either by using a sleeve of a material with high back scatter properties and a clear liquid in the balloon or a highly scattering liquid in a transparent balloon. In any case absorption losses in the balloon walls and the liquid are to be minimized. If a clear liquid is used, the back scatter capability of the balloon must be large compared to its transmissivity. If a light scattering liquid is to be utilized, "Intralipid" (manufactured by Fresenius AG) may be employed for filling the sleeve to generate the balloon.

Figure 3:
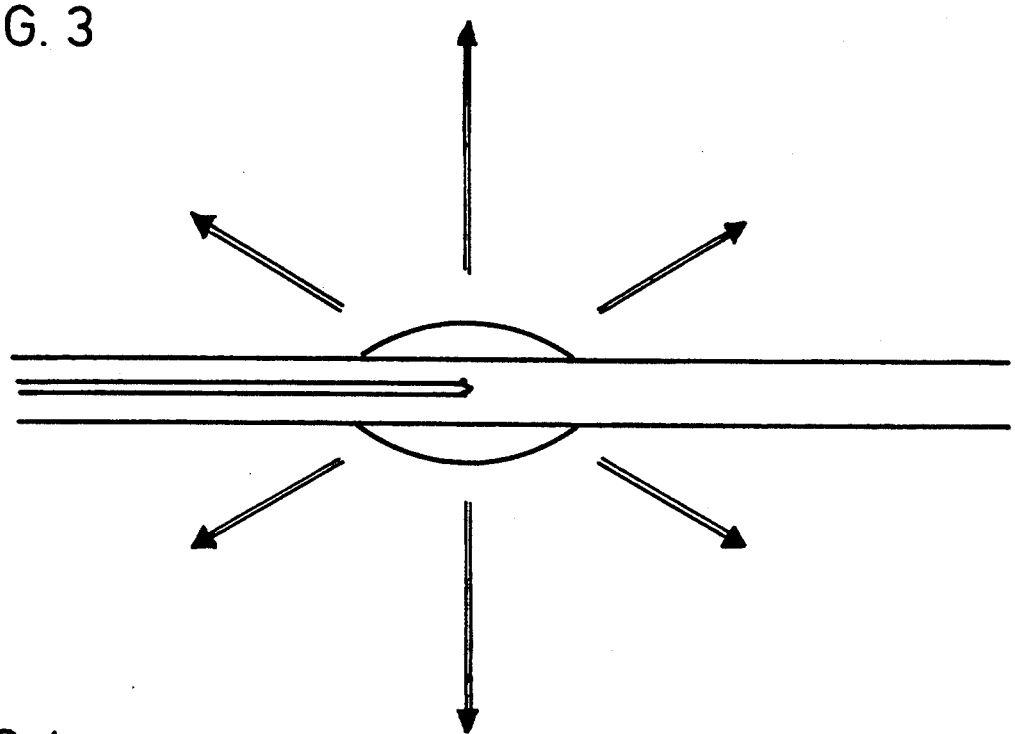
FIGS. 3 and 4 show scattering balloons of non-spherical shapes.
Figure 4:
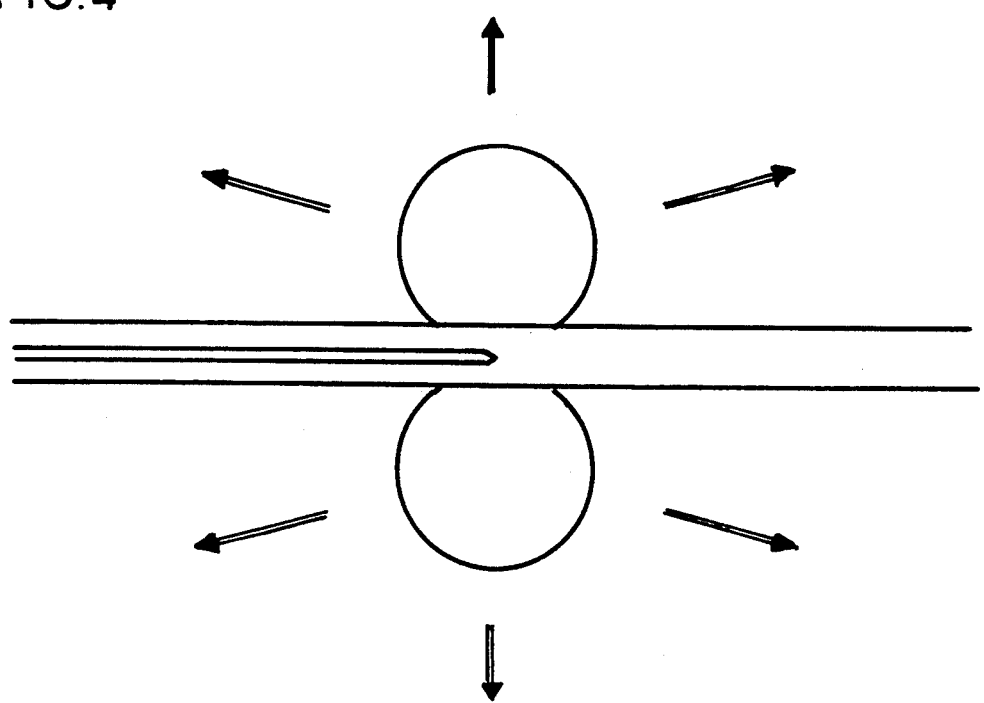

Especially if a scattering liquid is utilized in a transparent balloon the light emission characteristics can be influenced by the size and the shape of the balloon. A balloon which is only slightly filled and therefore is about cigar-shaped as shown in FIG. 3 provides for preferably radial light emission whereas a highly filled balloon which is torus-shaped as shown in FIG. 4 provides for more light emission in axial direction. The intensity of the light emission is indicated in the figures by the length of the arrows. It is therefore possible to uniformly irradiate the interior walls of hollow organs with cavities of various shapes, that is, with elongated or lenticular cavities. In order to obtain the proper balloon shape, the required fill volume must be determined before insertion of the catheter and after catheter insertion the appropriate amount of fill liquid must be admitted by way of a suitable metering device. The remaining organ cavity around the balloon is to be filled with an optically clear fluid, suitably by way of a second fluid admission channel.

In order to achieve good illumination of the cavity walls adjacent the catheter, the diameter of the scattering body must be substantially larger than the diameter of the catheter (about 3 times). On the other hand it should be substantially smaller than the cavity diameter (also about 3 times) in order to permit unrestricted redistribution of the light reflected from the cavity walls throughout the cavity. This provides for a homogenization effect in the light distribution, that is, for highly uniform light distribution, and results in a relatively high position tolerance for the central light source, In case of a bladder irradiation, for example, the diameter of the catheter is 6 mm, that of the balloon is 20 mm and that of the bladder cavity is 80 mm.

Figure 5:
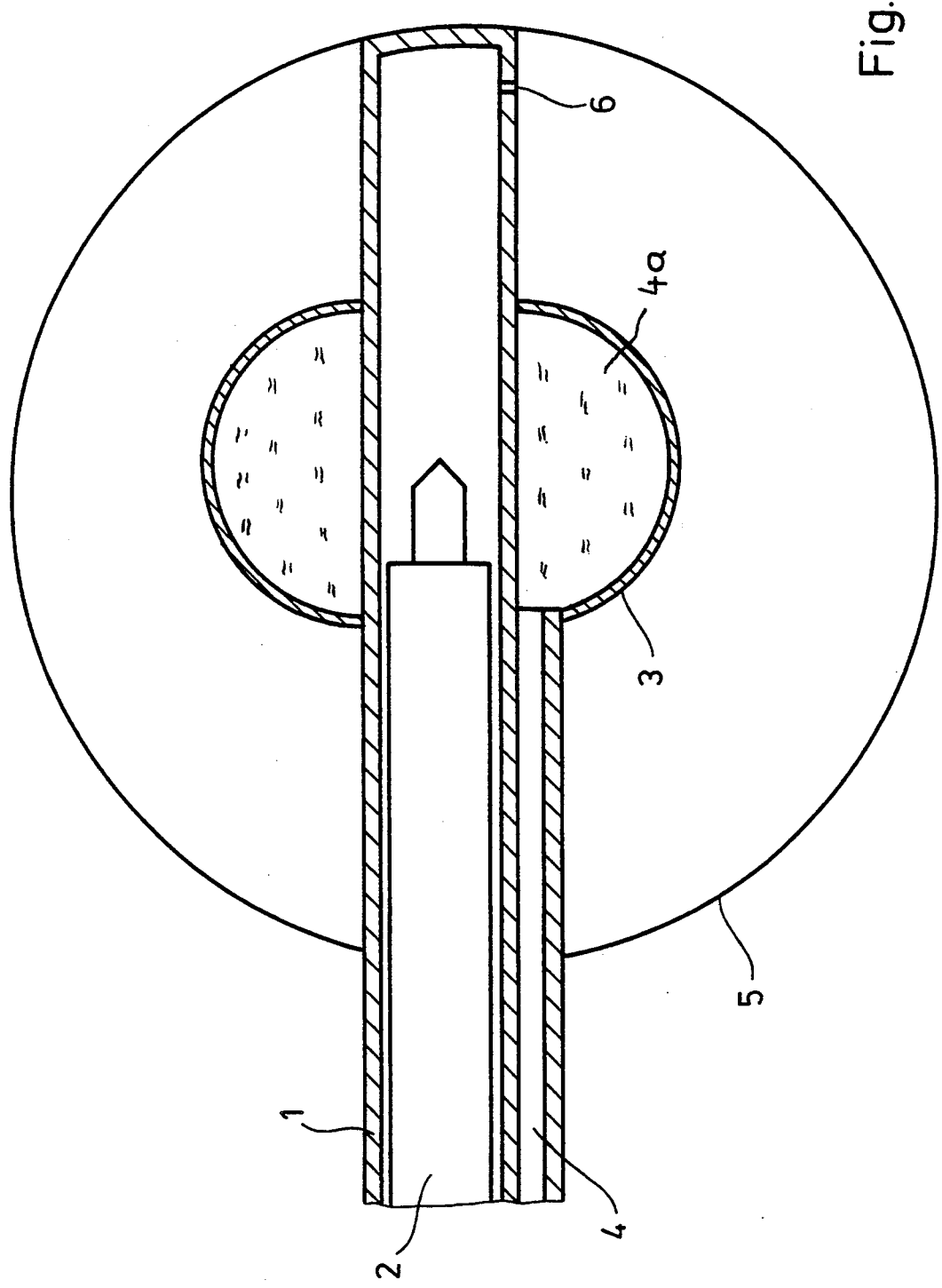
FIG. 5 shows an arrangement with centering structure.

In order to insure accurate centering of the scattering body, the catheter as shown in FIG. 5 may include a transparent positioning balloon 5 which encloses the balloon sleeve 3 and which, after insertion of the catheter, is filled, by way of an admission channel, with an optically clear fluid so that the positioning balloon fully fills the organ cavity. As shown in FIG. 5 the clear fluid admission channel may be the channel receiving the optical fiber 2 with which the positioning balloon is in communication by way of an opening 6 in the fiber channel wall.

LISTING OF REFERENCE NUMERALS

1 Catheter
2 Light conducting fiber
3 Resiliently expandable sleeve
4 Fluid line
5 Positioning balloon
6 Opening

What is claimed is:

1. Apparatus for isotropic irradiation of cavity walls, said apparatus comprising an axially rigid catheter including a first channel, a light conducting fiber disposed in said first channel so as to be movable therein, said fiber having a conically shaped tip with a cone angle adapted to deflect a light beam supplied through said conducting fiber essentially in radial outward direction, a resiliently expandable sleeve tightly surrounding said catheter and being at opposite ends thereof in sealing engagement with said catheter so that, upon expansion of said sleeve, the fiber tip remains in the center thereof, said catheter having a second channel in fluid communication with the space surrounded by said sleeve for admission of fluid thereto to expand said sleeve, depending on the amount of fluid admitted, to an oval to torus shape so as to form a light scattering structure whose distribution characteristic for light emitted from the light conductor tip disposed within the expanded sleeve is adjustably dependent on the degree of sleeve expansion.

2. An apparatus according to claim 1, wherein the cone angle of said tip is between 75° and 95°.

3. An apparatus according to claim 1, wherein the light scattering structure includes a liquid disposed in the sleeve and used to expand the sleeve.

4. An apparatus according to claim 1, wherein said fluid is a transparent liquid and said sleeve consists of a light scattering material.

5. An apparatus according to claim 1, wherein a positioning balloon is disposed around the catheter centrally about said sleeve and means are provided for filling said balloon with an optically clear fluid for centering said catheter in said cavity.

* * * * *